US00PP25813P3

(12) United States Plant Patent
Ranney

(10) Patent No.: US PP25,813 P3
(45) Date of Patent: Aug. 18, 2015

(54) ***ALBIZIA JULIBRISSIN* TREE NAME 'NCAJ1'**

(50) Latin Name: *Albizia julibrissin*
Varietal Denomination: NCAJ1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 133 days.

(21) Appl. No.: 13/987,977

(22) Filed: Sep. 20, 2013

(65) Prior Publication Data

US 2015/0089696 P1 Mar. 26, 2015

(51) Int. Cl.
*A01H 5/12* (2006.01)

(52) U.S. Cl.
USPC ..... Plt./216

(58) Field of Classification Search
USPC ..... Plt./216
See application file for complete search history.

*Primary Examiner* — Anne Grunberg

(74) *Attorney, Agent, or Firm* — Myers Bigel Sibley & Sajovec, P.A.

(57) ABSTRACT

'NCAJ1' is a new *Albizia julibrissin* tree particularly distinguished by a pendulous habit, burgundy foliage, and pinkish flowers.

3 Drawing Sheets

Latin name of the genus and species: The Latin name of the novel plant variety disclosed herein is *Albizia julibrissin.*

Variety denomination: The inventive variety of *Albizia julibrissin* disclosed herein has been given the varietal denomination 'NCAJ1'.

BACKGROUND OF THE INVENTION

The present invention relates to a new and distinct cultivar of silk tree botanically known as *Albizia julibrissin* 'NCAJ1' and hereinafter referred to by the cultivar name 'NCAJ1'. This new cultivar has a pendulous habit, burgundy colored foliage and pinkish flowers.

This new *Albizia julibrissin* was developed through a breeding program by the inventor in Mills River, N.C. 'NCAJ1' is an open pollinated seedling collected from *Albizia julibrissin* H2005-013-004. H2005-013-004 was a controlled cross between *Albizia julibrissin* 'Pendula' (not patented) and *A. julibrissin* 'Summer Chocolate' (U.S. Plant Pat. No. 13,822) that was planted in an isolation block of similar $F_1$ hybrids. The first asexual propagation of 'NCAJ1' was carried out in the fall of 2009 by root cuttings in Mills River, N.C. and has been asexually reproduced repeatedly by root cuttings in North Carolina since that time. 'NCAJ1' has been found to retain its distinctive characteristics through successive generations of asexual propagation

SUMMARY OF THE INVENTION

The following are the unique and distinguishing characteristics of this new cultivar when grown under normal horticultural practices in Mills River, N.C.

1. Pendulous habit; and
2. Dark burgundy mature foliage.

BRIEF DESCRIPTION OF THE DRAWINGS

The accompanying photographs show specimens of the new cultivar. The colors shown are as true as can be reasonably obtained by conventional photographic procedures. Colors in the photographs may differ slightly from the color values cited in the detailed botanical description, which accurately describe the colors of the new *Albizia julibrissin* cultivar. The photographs were taken in Mills River, N.C.

DETAILED BOTANICAL DESCRIPTION

Figure 1:
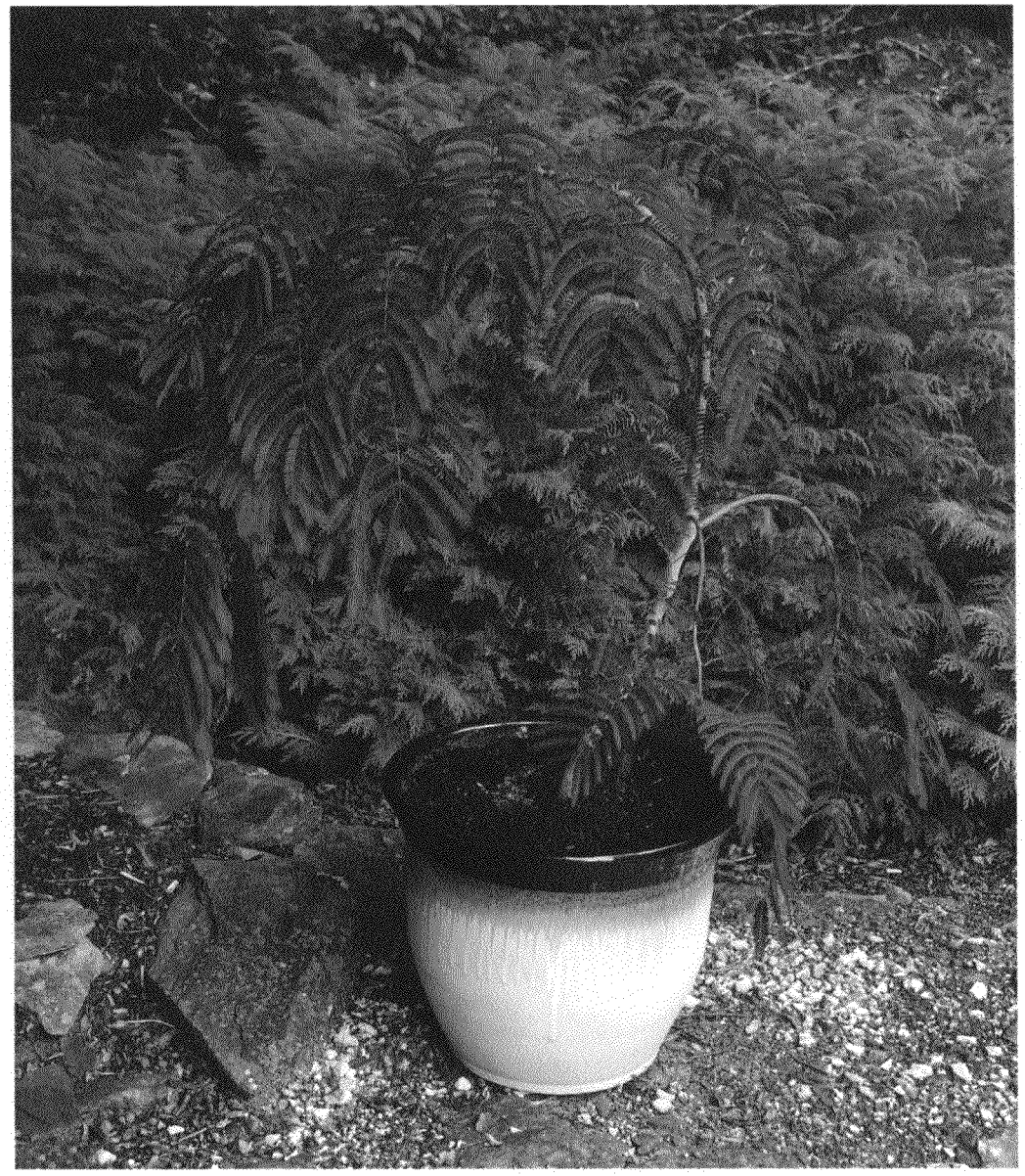
FIG. 1 shows the pendulous habit of 'NCAJ1'.
Figure 2:
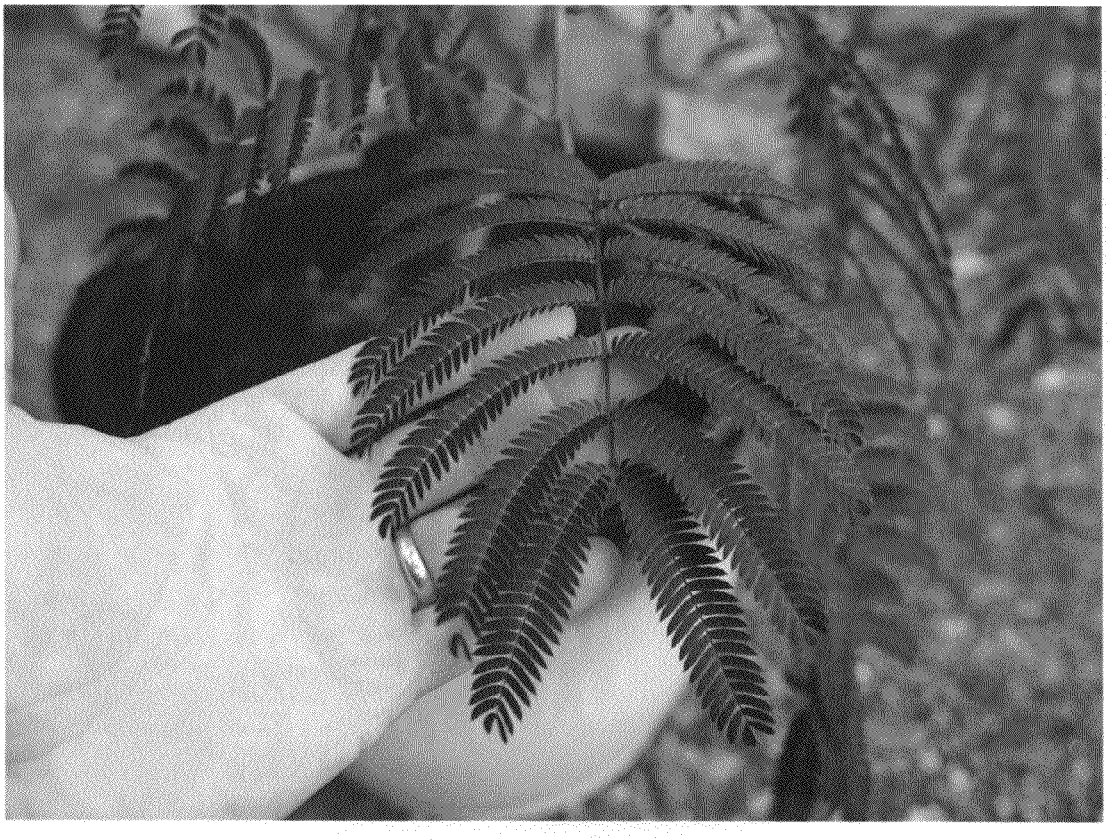
FIG. 2 shows the dark burgundy mature foliage of 'NCAJ1'.
Figure 3:
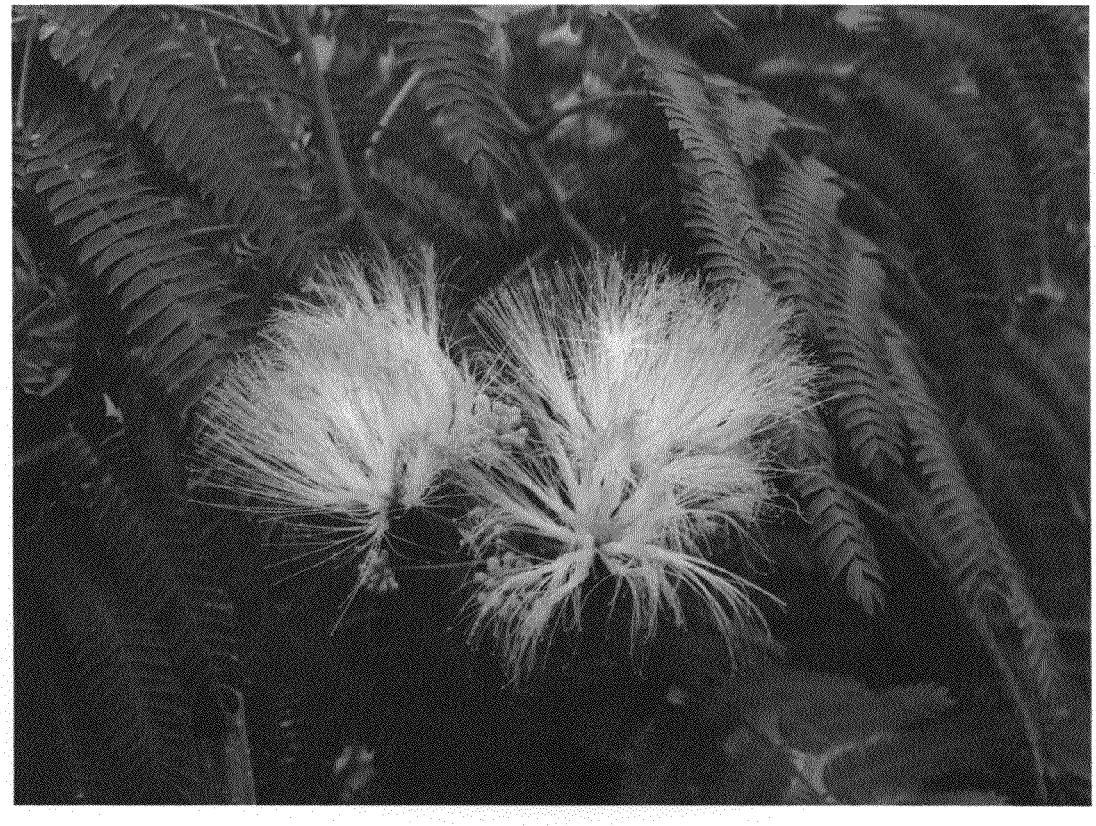
FIG. 3 shows the flowers of 'NCAJ1'.

The following is a detailed description of the botanical characteristics of the new and distinct variety of 'NCAJ1'. The detailed description was taken on a 2-year-old container plant grown in full sun with drip irrigation in Mills River, N.C. in August 2010. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable. Phenotypic expression may vary with light intensity, cultural, and environmental conditions.

Technical Description of the Variety

Classification:

*Botanical name.*—*Albizia julibrissin* 'NCAJ1'.

*Common name.*—Silk tree.

Parentage:

*Female parent.*—*Albizia julibrissin* NCSU H2005-013-004.

*Male parent.*—Open pollinated.

Plant description:

*Size.*—Approximately 2-3 m tall and about 1-2 m wide at maturity.

*Growth habit*.—Pendulous. Must be staked and trained initially to develop a tree form.

Leaves:

*Type*.—Bipinnately compound with about 12 to 24 pinnae. Each pinnae consisting of on average about 48 (range about 8 to 66) leaflets.

*Persistence*.—Deciduous.

*Arrangement*.—Alternate.

*Leaf size*.—Approximately 35 cm (range about 28 to 41 cm) long and about 20 cm (range about 13 to 24 cm) wide.

*Leaf attachment*.—Petiolate.

*Petiole*.—Color: Adaxial (upper) surface: RHS N186C (Greyed Purple). Abaxial (lower) surface: RHS N138B (Green).

*Stipules*.—None noted.

*Rachilla*.—Color: Adaxial (upper) surface: Closest RHS N186A (Greyed Purple). Abaxial (lower) surface: Closest RHS 148A (Yellow Green). Texture: glabrous.

Leaflet:

*Apex*.—Abruptly acute to apiculate.

*Base*.—Obliquely truncate.

*Length*.—Approximately 0.5 to 1.5 cm.

*Width*.—Approximately 2 to 4 mm.

*Margin*.—Entire.

*Color*.—Immature leaflet color: New leaves emerge green. Adaxial (upper) surface: RHS 143B (Green). Abaxial (lower) surface: RHS 143B (Green). Mature leaflet color: Adaxial (upper) surface: RHS N186A (Greyed Purple). Abaxial (lower) surface: RHS 191A (Greyed Green). Apex: N186C (Greyed Purple).

*Texture*.—Adaxial (upper) surface: Glabrous. Abaxial (lower) surface: Ciliate.

Stem:

*Immature* (*current season's growing shoot*).—Bark texture: Glabrous. Bark color: Greyed-green ranging from RHS 191 to 197. Lenticles: Greyed Orange (168D).

*Mature* (*prior year's shoot*).—Bark texture: Rugulose, glabrous. Bark color: Greyed-green (RHS 195). Lenticles: Greyed-orange (168D).

Inflorescence:

*Flowering season*.—Summer.

*Fragrance*.—Slight sweet fragrance.

*Inflorescence type*.—Compound corymb of heads, composed of about 15 to 20 sessile flowers per head.

*Flower form*.—Each flower consists of a 5 parted calyx (color RHS 151A) fused into a tube about 2-4 mm long and a 5 parted deeply lobed funnel form gamopetalous corrola about 5-15 mm long. Each flower has numerous stamens (average of about 26) that have connate filaments on the proximal end and are conspicuously elongate distally with minute anthers.

*Flower head size*.—Approximately 14 mm in diameter at balloon stage and approximately 75 mm at anthesis.

*Flower size* (*excluding stamen*).—Approximately 7 to 13 mm long.

*Color*.—Floral tube — Near Yellow-Green Group 151C.

*Peduncle*.—Color: Burgundy Red Purple Group 59B. Texture: Glabrous. Size: Average 24 mm (Range about 19 mm to 33 mm).

*Reproductive organs*.—Stamens: Quantity per flower: Variable, Average of about 26 (range about 21 to 32). Shape: Filament. Color: Base: Near White Group 155D. Distal end: Red purple ranging from 68A to 63B. Length: Average 30.7 mm (range 25.6 to 35.4 mm). Width: Less that 0.5 mm. Pistil: Quantity per flower: 1. Shape: Filament. Color: RHS 155D (near white). Length: Same length or slightly longer than stamens.

Fruit/seed: Fruit and seeds have not been observed.

Hardiness: USDA Zone 7-10.

Disease and insect resistance: No resistance or susceptibility to pests or disease problems beyond that of the species has been noted.

Comparison with other cultivars: The new variety differs from its parent and all other cultivars of *Albizia julibrissin* in having both burgundy foliage and a pendulous habit.

What is claimed is:

1. A new and distinct variety of *Albizia julibrissin* tree named 'NCAJ1,' substantially as illustrated and described herein.

* * * * *